(12) United States Patent
Fumex

(10) Patent No.: US 6,511,498 B1
(45) Date of Patent: Jan. 28, 2003

(54) SURGICAL BONE ANCHORING DEVICE

(75) Inventor: Laurent Fumex, 40, rue des Grands Meurgers, 78730 Saint-Arnoult-en-Yvelines (FR)

(73) Assignee: Laurent Fumex, Saint-Arnoult-en-Yvelines (FR)

( * ) Notice: Subject to any disclaimer, the term of this patent is extended or adjusted under 35 U.S.C. 154(b) by 0 days.

(21) Appl. No.: 09/601,740

(22) PCT Filed: Feb. 3, 1999

(86) PCT No.: PCT/FR99/00231
§ 371 (c)(1), (2), (4) Date: Aug. 7, 2000

(87) PCT Pub. No.: WO99/39644
PCT Pub. Date: Aug. 12, 1999

(30) Foreign Application Priority Data

Feb. 6, 1998 (FR) .............................. 98 01415

(51) Int. Cl.$^7$ .............................. A61B 17/04
(52) U.S. Cl. ............................. 606/232
(58) Field of Search ............ 606/232, 74, 215–216, 606/233; 24/129 D, 17 B

(56) References Cited

U.S. PATENT DOCUMENTS

| | | | | |
|---|---|---|---|---|
| 3,659,597 A | * | 5/1972 | Wolfers | 128/839 |
| 3,810,456 A | * | 5/1974 | Karman | 128/830 |
| 4,489,446 A | * | 12/1984 | Reed | 137/846 |
| 5,061,277 A | * | 10/1991 | Carpentier et al. | 623/2.36 |
| 5,123,914 A | * | 6/1992 | Cope | 606/108 |
| 5,403,348 A | * | 4/1995 | Bonutti | |
| 5,423,860 A | * | 6/1995 | Lizardi et al. | |
| 5,545,178 A | * | 8/1996 | Kensey et al. | |
| 5,569,269 A | * | 10/1996 | Hart et al. | 112/169 |
| 5,573,542 A | * | 11/1996 | Stevens | 112/169 |
| 5,584,695 A | * | 12/1996 | Besselink et al. | |
| 5,674,279 A | * | 10/1997 | Wright et al. | 623/2.37 |
| 5,716,397 A | * | 2/1998 | Myers | 606/1 |
| 5,980,539 A | * | 11/1999 | Kontos | 606/144 |
| 5,989,252 A | * | 11/1999 | Fumex | 606/72 |
| 6,183,461 B1 | * | 2/2001 | Matsuura et al. | 604/502 |
| 6,245,081 B1 | * | 6/2001 | Bowman et al. | 606/148 |

FOREIGN PATENT DOCUMENTS

EP 0 611 551 A * 8/1994

* cited by examiner

Primary Examiner—David O. Reip
Assistant Examiner—D Jacob Davis
(74) Attorney, Agent, or Firm—Burns, Doane, Swecker & Mathis, L.L.P.

(57) ABSTRACT

A bone anchoring device including a thread (1) whose middle part is in the form of a closed loop (2), and a deformable sleeve (5) which can slide on the thread (1) within the limits of the closed loop (2), wherein the deformable sleeve (5) can be deform into a ball by traction exerted on at least one strand (3, 4) of the thread (1).

15 Claims, 2 Drawing Sheets

SURGICAL BONE ANCHORING DEVICE

BACKGROUND OF THE INVENTION

1. Field of the Invention

The present invention relates to a surgical device for bone anchoring, and more particularly to a surgical device permitting simple and effective anchoring of suture thread or surgical thread on a bone support, in particular in orthopedic surgery, trauma surgery, gynecological surgery and cancer surgery.

2. Description of the Related Art

Tearing of tendons or of ligaments is something which can happen to many individuals of all ages, whether active or inactive, following traumas or excessive strains. The reparative surgical techniques currently used consist in attaching the tendon, by means of a suture thread, to a screw, a peg or a piton fixed in the adjoining bone.

To do this, the conventional technique consists in boring, in the bone, either a tapped hole, so that a screw or piton can be screwed into it, or an untapped hole receiving a peg which can be locked in the bone. The screw, the piton or the peg serves as an anchoring means on which one then attaches a suture thread which is used to re-attach the tendon which has been torn from its bone support. In other techniques, after a hole has been bored which is able to receive an anchoring piton, the suture thread is passed through the eye of the anchoring piton, then the latter is introduced into the hole by means of a special instrument, and finally the tendon to be fixed is sutured. An example of an anchoring screw for fixing tissues by means of a suture thread is described in the patent U.S. Pat. No. 5,443,482.

Depending on the circumstances, the operations can be performed by open surgery or by closed surgery using celioscopy or arthroscopy procedures. Surgical techniques using devices of this type are described, for example, by F. A. Barber et al., *J. of Arthroscopy and Related Surgery*, vol. 11, No. 1, pages 21 to 28 (1995).

The patent U.S. Pat. No. 5,403,348 describes a bone-anchoring device comprising a rigid cylindrical component with a surgical thread passing along its axis, which is introduced into a hole bored in the bone, as far as the spongy substance. By acting on the thread, the orientation of the cylindrical component is modified in such a way as to block it under the solid superficial layer of the cortical bone, deforming the spongy substance.

The patent EP-A-611,551 describes an anchoring device for a suture thread, including a rivet intended to be fixed in the bone support, formed by two elements: a spike, and a rigid sleeve in which it can slide. Another anchoring device is described in the patent U.S. Pat. No. 5,584,695, comprising a rivet with shape memory, capable of being introduced in the cold state into the bone support and of expanding in the hot state so as to cause blocking.

These known devices have various disadvantages. They are highly invasive and are non-absorbable, and their positioning involves techniques which are often awkward to perform. Moreover, some of the known devices include items containing allergenic materials, for example certain shape-memory materials, and according to some authors these materials are sometimes carcinogenic. In addition, a large number of screws, pegs or pitons, of accessories for boring into the bone and of accessories for positioning the anchoring means must be available in various sizes so as to be able to respond to all situations.

SUMMARY OF THE INVENTION

The subject of the present invention is a bone-anchoring device which necessitates only the prior boring of a single hole with any wall shape, without requiring tapping, and permitting fixation of organs such as tendons and ligaments, or suspension of the cervix of the uterus, using a surgical thread or a suture thread without the need to use a means of the screw or piton type.

The invention also describes an ancillary instrument specially adapted for placing the aforementioned anchoring device in position.

The anchoring device according to the present invention can be used in combination with a hole bored in the bone support, and it comprises a deformable tubular sleeve, associated with means capable of deforming it between a first stretched position of small diameter and a second folded position of greater diameter.

The length of the tubular sleeve in the stretched position must be substantially greater than the diameter to ensure maximum efficacy of the device. More precisely, the length of the sleeve must be equal to at least 5 times the diameter, and preferably at least ten times the external diameter of the sleeve.

According to the invention, the means capable of deforming the sleeve are made up of a thread passing through the deformable tubular sleeve along its axis and forming a closed loop, the tubular sleeve being located on the thread, in the loop-shaped part. The internal diameter of the sleeve must be sufficient to contain the thread without causing too great a frictional force. By way of example, a tubular sleeve can be used having a length of between about 15 and 30 mm, an external diameter of between 1 and 2 mm, and an internal diameter of between 0.6 and 1.2 mm.

Thus, in its preferred embodiment, the boneanchoring device of the invention comprises a thread having a middle part intended to be introduced into the hole bored beforehand, having a closed loop shape, bearing on the loop-shaped part a deformable tubular envelope or sleeve which is able to slide on the thread within the limits of the loop. The closure of the loop can be obtained by simple crossing of the two strands of the thread, on either side of the deformable sleeve. The tubular sleeve can be deformed into a ball by simple traction exerted on at least one strand of the thread.

According to the present invention, the thread used is preferably a surgical thread or a suture thread, absorbable or non-absorbable, of the type used to fix or re-attach organs. For example, it is possible to use a polyester thread such as the one marketed under the brand name Ercylene®, or a polyamide thread such as Trynil®. Thus, the thread serves both for causing deformation of the tubular sleeve and also for fixation of the organs.

The tubular envelope or sleeve capable of sliding on the thread in the loop has a total length which is less than or equal to about twice the depth of drilling in the bone, and a diameter which is less than or equal to that of the hole bored in the bone. Thus, the loop bearing the sleeve is fully introduced into the hole bored in the bone. This sleeve can advantageously be made of any deformable material, preferably one which has a certain elasticity, which has the property of being implantable, and which is absorbable or non-absorbable (for example a braided metal or plastic wire, a tube made of polyester or polyamide, or a tube made of silicone).

Depending on the circumstances, the sleeve can be made up of a single element or of several elements.

At the time of positioning, after introduction of the sleeve and of the thread into the hole bored in the bone, when the loop is tightened by pulling on at least one of the two strands of the thread, the latter is applied against the sleeve and causes its deformation, changing it from a first stretched position to a second position in which it is folded on itself and in which its cross section is increased. More precisely, having folded the sleeve at its middle in such a way that the strands of the thread emerge in the same direction, and having introduced it thus into the hole bored in the bone, by exerting a traction on the strands of the thread in diverging directions, the sleeve is folded until it presents approximately the form of a ball which, because its diameter is greater than that of the sleeve, is compressed against the walls of the hole into which the sleeve has been introduced. By reason of this pressure, the device is then held firmly in the hole bored in the bone.

According to a simple embodiment, the sleeve in the form of a linear cylinder is slipped onto the thread, and the loop is then formed around the sleeve.

In another simple embodiment, the sleeve can be preformed in a U shape and the thread passes into the sleeve via one of its two open ends, emerges via the second end and forms a loop before passing again into the sleeve via the first end in order to exit via the second end. In one variant, the sleeve can include an orifice extending through its wall near each of the two ends, and the thread can pass into the sleeve, then emerge therefrom via one or other of its orifices. In this latter embodiment, if the orifices are arranged asymmetrically with respect to the center plane of the loop, the traction exerted on the strands of the thread in order to cause compression of the sleeve also results in a tilting effect which adds to and reinforces the friction and blocking against the inner walls of the hole bored in the bone.

These orifices are arranged symmetrically with respect to the middle of the deformable sleeve, near to the ends, or in its central part. It is preferable to provide two orifices arranged in the same diametrical plane of the sleeve.

According to another embodiment of the invention, the sleeve is in the form of a toric ring which has at least one orifice extending through its wall for the passage of the two strands of the thread. In this alternative embodiment, the thread passes into the sleeve via the orifice, forms a complete loop along the inside of the annular sleeve, and emerges via the same orifice.

The sleeve is preferably reinforced in the zone where the thread passes into it, that is to say on the periphery of each of its ends, or around the orifices made in its wall, as appropriate. This reinforcement can be obtained, for example, by providing an extra thickness of material or by adhesive bonding or welding of a strip having greater strength.

The tubular sleeve can be open at its two ends, or by contrast can be closed. In this case, it includes at least two orifices in its wall for the passage of the strands of the thread. The wall of the tubular sleeve is preferably traversed by at least two orifices for the passage of the strands of the thread, these orifices being arranged in such a way that the traction exerted on the strands of the thread causes a tilting movement of the sleeve, promoting its anchoring against the walls of the hole bored in the bone.

The ancillary instrument for positioning the anchoring device according to the present invention essentially comprises a rod capable of carrying the thread and its sleeve for introducing them into the hole bored in the bone, as well as a slotted cylindrical component enclosing the thread and the sleeve and capable of sliding on the rod along a distance corresponding to the depth of the hole.

According to a preferred embodiment, the sliding of the cylindrical component is guided by a rib formed on the rod and cooperating with the slot.

According to another characteristic of the present invention, the ancillary instrument comprises a handle which is integral with the rod and which has a grip part facilitating its manipulation.

The sliding cylindrical component is made of a material compatible with use in a surgical environment.

The ancillary instrument for positioning of the anchoring device of the invention is easily used by introducing the point of the rod of the ancillary instrument, bearing the loop-shaped thread and its sleeve, into the hole bored beforehand in the bone, until the loop is fully engaged in the hole. After withdrawing the point from the hole, while leaving the thread and sleeve therein, it then suffices to exert a traction on one strand of the thread, while slightly holding the other strand still in order to cause tightening of the loop inside the hole in the bone and deformation of the sleeve on the loop until it adopts the shape of a ball, the diameter of which is greater than that of the tubular sleeve before deformation. With the traction being continued until locking occurs, the deformed sleeve then finds itself compressed against the inner walls of the cavity.

The two strands of the thread can then be knotted, at the edge of the hole bored in the bone, in order to lock the device and prevent its loosening, then, if necessary, attach the tendon or organ using the strands of the thread. Moreover, when the sleeve is folded into a ball shape, as indicated above, the enlargement of its diameter compared to the initial diameter of the sleeve, and the pleated shape of its surface, increase the phenomenon of anchoring in the spongy substance of the bone, resulting in improved fastening of the device of the invention in the bone.

As has been indicated above, the device and the ancillary positioning instrument according to the present invention are most particularly intended for reparative surgery of ligaments and tendons. The invention can also be used in gynecology, for example for fixing the uterus to the sacrum by way of a ligament.

The device of the invention is also suitable for cancer surgery, and in this application a thread is used which can contain a radioactive substance such as iridium. The thread is placed in the tumor, preferably using a non-absorbable thread, and the latter can serve as a marker for secondary ablation of the tumor.

Tests conducted with the anchoring device according to the present invention, carried out under experimental conditions, have revealed excellent properties of fixation and resistance to traction, comparable to, or even better than, those of the best of the known devices of the prior art.

The tests were conducted on two series of devices made up of sleeves of non-absorbable polyester braid with heat-bonded ends, of length equal to 20 mm for the 1st series, and 30 mm for the 2nd series. The sleeves have an external diameter of 1.6 mm and an internal diameter of 1.0 mm. A polyester suture thread measuring 0.5 mm in diameter (USP 2) is slipped inside the sleeve. The ends of the thread are knotted in order to form a loop.

The sleeves bearing the thread are introduced into a series of holes measuring 2.3 mm in diameter and 19 mm (sleeves of 30 mm) or 11 mm (sleeves of 20 mm) in depth, bored in a fresh human humerus. The tests on resistance to pullingout in the axis of the hole are carried out using an Adamel Lhomargy DY 34 universal traction machine equipped with a calibrated 1 kN cell. A cylindrical bar integral with the mobile crosspiece of the machine is passed into a loop closed at the other end of the sample. The speed of displacement of the crosspiece is 5 mm/min. The tests are carried out until the device is torn from the bone support or the thread breaks.

In all cases, the suture thread was seen to break without the sleeve being pulled out of the hole bored in the bone. The force of resistance to pullingout varies between 10.2 and 12 kg for the samples in the two series.

BRIEF DESCRIPTION OF THE FIGURES OF THE DRAWING

The characteristics and advantages of the present invention will become clearer in the following examples which relate to preferred embodiments, with reference being made to the attached drawings which depict.

DETAILED DESCRIPTION OF THE PREFERRED EMBODIMENTS

Figure 1:
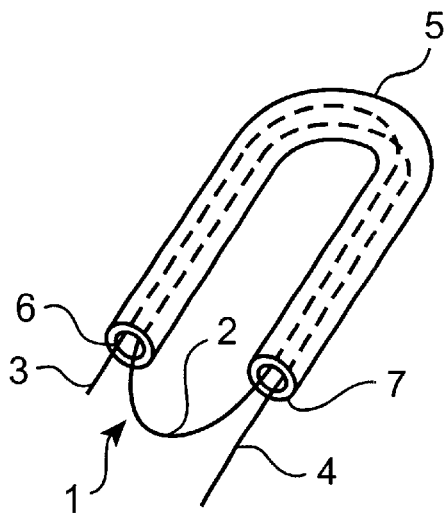
FIG. 1: a diagrammatic view of a fixation thread according to the present invention, introduced into a U-shaped sleeve, before tightening and deformation.

FIG. 1 shows the anchoring device of the present invention, which comprises a suture thread (1) forming, in its middle part, a closed loop (2) which is capable of being tightened by simple traction on one of the two strands (3, 4) of the thread (1).

The thread (1) forming the loop (2) passes into the sleeve (5) via its end (6), emerges via the other end (7), once again enters via the end (6) and emerges via the end (7) in such a way as to form a complete loop in the sleeve. The latter is made of deformable and compressible material, capable of sliding on the thread. The traction on the strands (3 and 4) of the thread brings about a decrease in the length of the loop (2) until its length becomes equal to that of the sleeve (5). Continuing the traction on the strands of the thread (1), or on only one of the strands while holding the other one still, results, on the one hand, in compression of the sleeve, whose surface forms undulations because of the compressibility of the material from which it is made, and, on the other hand, in tightening of the loop (2).

The edges of the sleeve, at each of its ends (6) and (7), are reinforced to prevent them from being notched by the thread (1) when the latter is tightened. This reinforcement is obtained here simply by increasing the thickness of material.

The device is put into position using an ancillary instrument such as the one described below. The method of positioning consists in folding via its center the loop (2) bearing the sleeve (5) in such a way that the two strands of the thread emerge in the same direction, as is shown in FIG. 1, and in introducing it via its center into the hole bored in the bone, then in tightening it by exerting a traction on the strands (3 and/or 4) of the thread (1) in divergent directions. It is preferable to introduce the entire loop into the hole, so that no part of the sleeve protrudes from the hole. The edges (6) and (7) of the sleeve are preferably inserted into the hole under the surface of the cortical bone.

When the loop (2) is tightened by pulling on the strand or strands (3) and (4) of the thread, it is narrowed and the flexible sleeve (5) is compressed inside the hole. Then, by further tightening by pulling on the strand (3) of the thread (1), the sleeve (5) is deformed until it adopts the shape of a ball. This ball will be unable to come out of the hole through which it has been introduced into the bone because its diameter has become markedly larger than that of the bored hole. Moreover, this ball bears on the inner face of the cortical bone or in the spongy bone if it is sufficiently hard.

It therefore suffices to choose a suture thread bearing a sleeve which has a length and a diameter permitting, by tightening of the loop (2), the formation of a ball which will bear on the hard inner face of a bone and whose diameter will be sufficiently large to withstand the stresses imposed on it.

Figure 2:
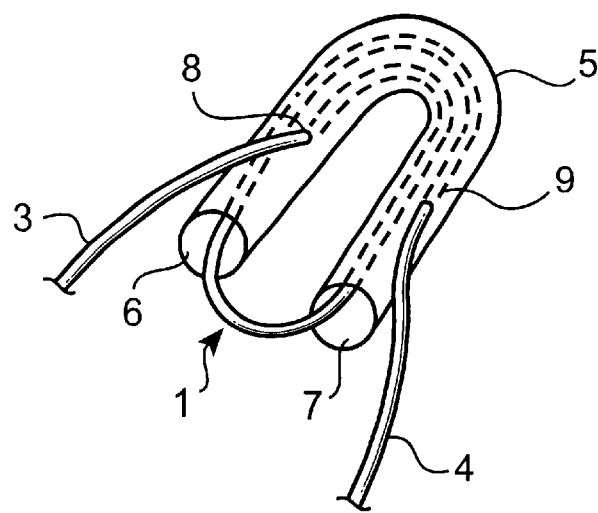
FIG. 2: a view of an alternative embodiment of the device in FIG. 1, where each strand of the thread emerges from the tubular sleeve through an orifice near each end.

In the alternative embodiment of the device represented in FIG. 2, instead of passing into the sleeve (5) via the ends (6) and (7), the thread (1) passes through the sleeve (6) via the orifices (8) and (9) provided near the ends of the sleeve. The two orifices (8) and (9) are preferably situated on the same side relative to a diametrical plane of the sleeve.

Figure 3:
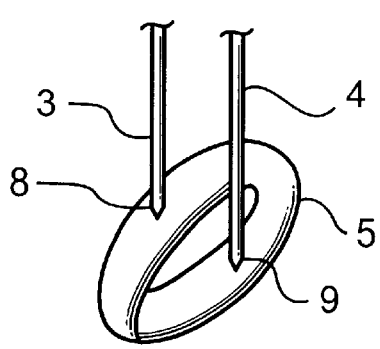
FIG. 3: a view of the device from FIG. 2 showing the shape adopted by the tubular sleeve after a first traction on the strands of the thread.

This embodiment makes it easier to fold the sleeve on itself to form a circle, as is represented in FIG. 3. When traction continues to be exerted on the strands of the thread, this circle deforms and the sleeve forms wrinkles to adopt substantially the shape of a ball.

Figure 4:
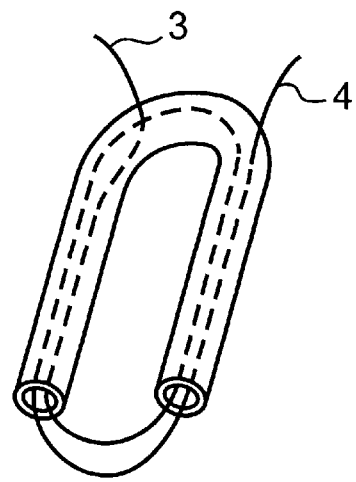
FIG. 4: a view of another alternative embodiment of the device of the invention.

FIG. 4 shows another alternative embodiment of the invention where the strands (3) and (4) pass through the wall of the sleeve (5) via the orifices (8') and (9') arranged like the orifices (8) and (9) of the device in FIG. 2, but near the central part of the sleeve. In this alternative embodiment, the strands of the thread are preferably directed in a direction opposite to that of the ends (6) and (7) of the sleeve, and the latter can be introduced into the hole bored in the bone via its ends and not via its center.

Figure 5:
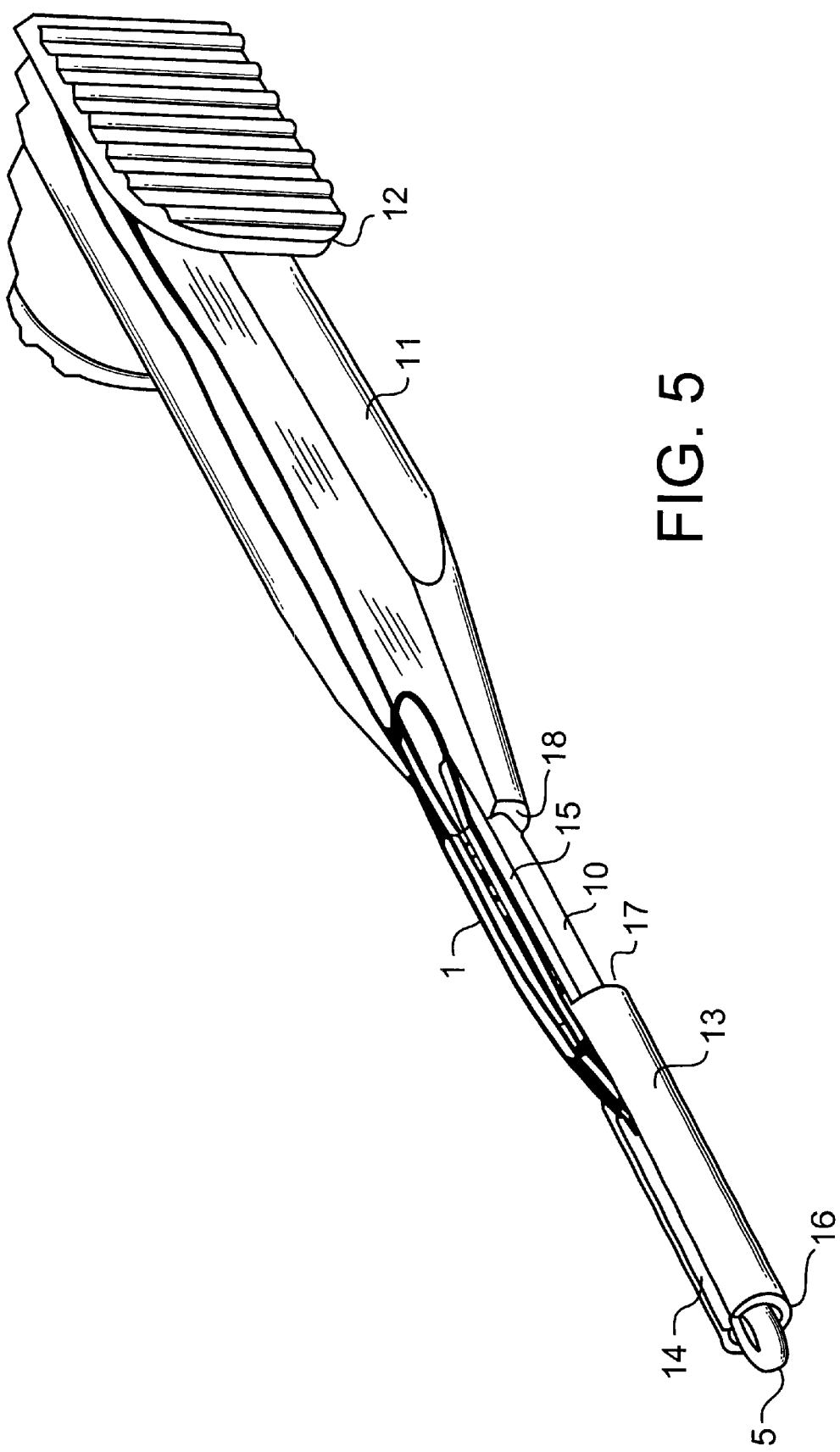
FIG. 5: a perspective view of an ancillary instrument permitting semi-automatic positioning of an anchoring device according to the invention.

The anchoring device described above is put into position effectively using an ancillary instrument according to the invention, represented in FIG. 5.

This figure shows a simple ancillary instrument making it easier to place the anchoring device in a hole which has been bored beforehand in a bone.

This ancillary instrument comprises a rod (10) intended to support the loop of the suture thread (1) in the sleeve (5), via the center of its loop (2), to ensure its positioning in the hole bored in the bone (not shown). As FIG. 4 shows, the thread (1) and its sleeve (5) are folded via their center on the free end of the rod (10). This rod (10) is fixed to a handle (11) bearing a grip part (12).

The rod (10), the sleeve (5) and the thread (1) are enclosed in a cylindrical component (13) which has a slot (14) along its entire length. This cylindrical component (13) can slide on the rod (10) and it is guided by the rib (15) which cooperates with the slot (14). The functioning is described below.

After the hole has been bored in the bone using a conventional instrument, the rod (10) bearing the loop-shaped thread (1) and the sleeve (5) is introduced into the hole in such a way that the distal edge (16) abuts against the bone, at the edge of the hole. The rod (10) is then inserted, which results in the sliding of the cylindrical element (13) along the rib (15) until the proximal edge (17) of the cylindrical element (13) comes to bear against the shoulder (18) situated at the base of the rod (10). The sliding distance is determined so as to correspond to the depth of the hole bored in the bone. In this position, the sleeve (5) is entirely inserted in the hole bored in the bone. The cylindrical element (13) may, if appropriate, be replaced by a longer or shorter element depending on the depth of boring.

The strands of the thread (1) which are fixed to thread-holder plates (not shown) integral with the handle (11) are then undone. The ancillary instrument is withdrawn from the hole by acting on the grip (11), then the strand (4) of the thread (1) is pulled in such a way as to slide the thread (1) in the sleeve (5) and to deform the latter so that it forms a ball.

The positioning of the anchoring device by means of the ancillary instrument in FIG. 5 is done as indicated above, in a semi-automatic manner.

What is claimed is:

1. A surgical device for anchoring a thread or wire to a bone having a hole bored therein, comprising:
    a deformable tubular sleeve which is capable of deforming between a first stretched position of low cross section and a second folded position of greater cross section; and a thread whose middle part is in the form of a closed loop passing through the deformable tubular sleeve, and wherein the deformable tubular sleeve is able to slide on the thread within the limits of the closed loop.

2. The device according to claim 1, wherein the sleeve can be deformed into a ball by traction exerted on at least one strand of the thread.

3. The device according to claim 1, wherein the length of the sleeve is less than or equal to twice the depth of the hole bored in the bone.

4. The device according to claim 2, wherein the length of the sleeve is less than or equal to twice the depth of the hole bored in the bone.

5. The device according to claim 1, wherein the diameter of the sleeve is less than or equal to the diameter of the hole.

6. The device according to claim 2, wherein the diameter of the sleeve is less than or equal to the diameter of the hole.

7. The device according to claim 3, wherein the diameter of the sleeve is less than or equal to the diameter of the hole.

8. The device according to claim 1, wherein the length of the sleeve is equal to at least 5 times the diameter of the sleeve.

9. The device according to claim 5, wherein the sleeve is made up of a single linear cylindrical element that is open at both of its ends.

10. The device according to claim 9, wherein the sleeve includes at least one orifice extending through its wall dimensioned for the passage of two strands of the thread.

11. The device according to claim 5, wherein the sleeve is made up of a toric ring and including at least two orifices for the passage of the strands of the thread.

12. The device according to claim 5, wherein the sleeve is made up of a toric ring having at least one orifice extending through its wall dimensioned for the passage of the strands of the thread.

13. The device according to claim 10, wherein the wall of the tubular sleeve has at least two orifices extending through it for the passage of the strands of the thread, these orifices being arranged in such a way that the traction exerted on the strands of the thread causes a tilting movement of the sleeve.

14. The device according to claim 11, wherein the wall of the toric ring has at least two orifices extending through it for the passage of the strands of the thread, these orifices being arranged in such a way that the traction exerted on the strands of the thread causes a tilting movement of the sleeve.

15. The device according to claim 12, wherein the wall of the tubular sleeve has at least two orifices extending through it for the passage of the strands of the thread, these orifices being arranged in such a way that the traction exerted on the strands of the thread causes a tilting movement of the sleeve.

* * * * *